United States Patent [19]

Green

[11] Patent Number: 4,613,699
[45] Date of Patent: Sep. 23, 1986

[54] PHOSPHINE OXIDES AND THEIR USE AS FLAME RETARDANTS IN STYRENE MODIFIED POLYPHENYLENE ETHER RESINS

[75] Inventor: Joseph Green, East Brunswick, N.J.
[73] Assignee: FMC Corporation, Philadelphia, Pa.
[21] Appl. No.: 707,366
[22] Filed: Mar. 1, 1985
[51] Int. Cl.⁴ .................................................. C07F 9/53
[52] U.S. Cl. ..................................... 568/15; 252/601; 524/129
[58] Field of Search ............................................ 568/15

[56] References Cited

U.S. PATENT DOCUMENTS

| | | |
|---|---|---|
| 3,257,357 | 6/1966 | Stamatoff . |
| 3,257,358 | 6/1966 | Stamatoff . |
| 3,267,149 | 8/1966 | Garner ............... 568/15 X |
| 3,306,874 | 2/1967 | Hay . |
| 3,306,875 | 2/1967 | Hay . |
| 3,400,163 | 9/1968 | Mason et al. . |
| 3,502,730 | 3/1970 | Mason et al. . |
| 3,639,506 | 2/1972 | Haaf . |
| 3,917,560 | 11/1975 | Hoffman . |
| 3,948,980 | 4/1976 | Dettmeier et al. ............... 568/15 X |
| 4,007,229 | 2/1977 | Hechenbleikner ............... 568/15 |
| 4,154,775 | 5/1979 | Axelrod . |
| 4,163,760 | 8/1979 | Elsner et al. . |
| 4,255,324 | 3/1981 | Granzow et al. . |
| 4,287,119 | 9/1981 | Braksmayer et al. . |

FOREIGN PATENT DOCUMENTS 923532 4/1963 United Kingdom ............... 568/15

OTHER PUBLICATIONS

Chemical Abstracts 60 12054f (1964).
Chemical Abstracts 60 12055 (1964).

Primary Examiner—Helen M. S. Sneed
Attorney, Agent, or Firm—Charles C. Fellows; Robert L. Andersen

[57] ABSTRACT

A phosphine oxide composition represented by the formula:

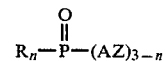

wherein P is phosphorus, O is oxygen, A is an alkylene chain of 2 to 12 carbon atoms, Z is a polar group, n is 1 or 2, and R is an ethylenically unsaturated alicyclic hydrocarbon or alcohol.

5 Claims, No Drawings

PHOSPHINE OXIDES AND THEIR USE AS FLAME RETARDANTS IN STYRENE MODIFIED POLYPHENYLENE ETHER RESINS

This invention relates to phosphine oxides and in particular to certain novel cyclic phosphine oxides as flame retardants in polyphenylene ether resins.

The polyphenylene ethers are a well-known class of linear thermoplastic engineering resins, the description and preparation of which are documented at length in the technical and patent literature; see U.S. Pat. Nos. 3,306,874 and 3,306,875 to Hay and U.S. Pat. Nos. 3,257,357 and 3,257,358 to Stamatoff. Generally speaking, polyphenylene ethers are combined with other polymers such as a polystyrene to provide modified polyphenylene ether resins. An important commercial grade polyphenylene ether engineering plastic contains about 35 to 85% by weight polyphenylene ether and about 65 to 15% by weight of a polystyrene resin. Such modified polyphenylene ether resins, with which the present invention is particularly concerned, are used extensively in the automotive and transportation industries as a replacement for metal to reduce vehicle weight. Makers of electrical/electronic equipment and appliances also use substantial quantities of such resins.

Styrene modified polyphenylene ether resins will burn if subjected to flame. To reduce their combustibility, such resins are formulated with a flame retardant additive of which a large number have been described. One well-known flame retardant is a blend of an aromatic halogen compound and an aromatic phosphate as disclosed in U.S. Pat. No. 3,639,506. A preferred composition in accordance with that teaching comprises from 20 to 80% by weight of poly(2,6-dimethyl-1,4-phenylene)ether, 20 to 80% by weight of a high impact polystyrene (styrene modified with rubber) and from 3 to 25 parts by weight per 100 parts by weight of the polyphenylene ether composition of a flame retardant combination of 1 part triphenyl phosphate and 3 to 4 parts of a heavily chlorinated biphenyl. U.S. Pat. No. 4,154,775 states that cyclic phosphates are, by themselves, an effective, non-plasticizing flame retardant additive for polyphenylene ether resins. Numerous other organic phosphates have been proposed and tested as flame retardants.

An improved class of fire retardant compounds for polyphenylene ether compositions are certain 3-hydroxyalkylphosphine oxides disclosed in U.S. Pat. No. 4,287,119. These compounds can be represented by the formula:

wherein $R_1$ is selected from the group consisting of hydrogen and methyl radicals, $R_2$ is an alkyl radical of 4 to 8 carbon atoms and n is either zero or one.

There are numerous problems associated with the development of a satisfactory flame retardant for plastics. In addition to its flame suppressing capacity, the flame retardant must be heat and light stable, noncorrosive, nontoxic, compatible, and not adversely alter the mechanical properties of the plastic.

One type of physical deformation that occurs in flame retardant thermoplastic resins, such as the polyphenylene ether compositions or resins mentioned herein, is known as stress cracking. During hot molding of the resin the flame retardant may juice, boil off or exude and condense on the mold and the surface of the resin. The plastic part may be under stress as a result of the molding and the condensed flame retardant may result in cracking of the molded part. Failure can occur during molding or on storage of the final manufactured article.

Stress cracking is particularly difficult to control when using organic phosphates as a flame retardant in styrene modified polyphenylene ether resins; juicing can be quite severe and phosphate esters readily crack stressed molded polyphenylene ether parts. Much less prone to cause stress cracking are the aforementioned hydroxyalkylphosphine oxides. These are generally excellent flame retardant additives although their thermal stability and ease of incorporation into the resin or compatibility with the resin are not as good as might be desired. Volatility can also be a factor with some of the lower boiling members.

Copending U.S. patent application Ser. No. 604,254 filed 4/26/84 discloses cyclic phosphine oxides which are the product of a three-step synthesis in which the first step is carried out by alkylating phosphine in the presence of a free radical source with an ethylenically unsaturated cyclic hydrocarbon of the formula:

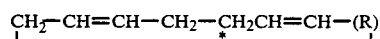

wherein R is $-CH_2-$, $-CH_2CH_2CH_2-$ or $-CH_2CH_2CH=CHCH_2-$ to produce a bicyclic phosphine containing a secondary phosphine group, PH as part of the cyclic phosphine ring structure. The so obtained part of the cyclic phosphine ring structure is then further alkylated with a 1-alkene having a polar group, whereby residual phosphine hydrogen atom is replaced by an alkyl radical containing the said polar group. This alkylated phosphine is then oxidized to the corresponding oxide. These phosphine oxides, while technically attractive and useful, are unfortunately high priced due to the relatively high cost of the ethylenicaly unsaturated cyclic hydrocarbons.

The present invention provides novel phosphine oxide products useful for flame retarding polystyrene modified polyphenylene ether polymers and novel flame retarded polyers containing flame retardant amounts of these novel phosphine oxide flame retarding products. The phosphine oxide products are made from phosphine and a diene, have a phosphorus content of at least 5%, preferably 8% or more, and contain a polar substituent.

The objective is to prepare a phosphine oxide with a single polar group. Because of the polarity of the flame retardant, it will not stress crack the resin. Too much polarity, such as when more than one polar group is present, may result in a product which is not compatible with the resin and is therefore difficult to process into the resin.

Therefore, bulky olefins and dienes are reacted with $PH_3$ to yield secondary phosphines, i.e., the reaction stops at the secondary phosphine stage due to steric hindrance. Subsequently the secondary phosphine is allowed to react with an olefin containing a polar group.

The novel phosphine oxides of this invention are the products of a two or three step synthesis in which the first step is conveniently carried out by alkylating phosphine in the presence of a catalyst with an olefin compound selected from:

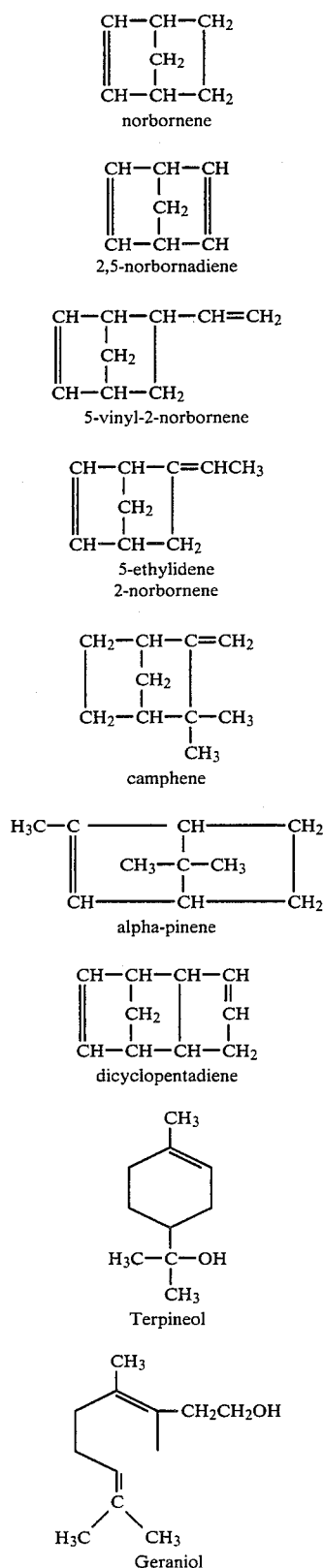

To produce compounds or mixtures of compounds of the formula $$R_n-\overset{\overset{O}{\|}}{P}-(AZ)_{3-n}$$

wherein O is oxygen, P is phosphorus, A is an alkylene chain of 2 to 12 carbon atoms, Z is a polar group and n is 1 or 2 and R is an ethylenically unsaturated alicyclic hydrocarbon or alcohol or geraniol.

Norbornylene, alpha pinene, camphene and dicyclopentadiene react to produce products in which one or two molecules of the cyclic compound reacts with phosphine. These and other reactive products of the invention are illustrated in Table 1 showing approximate percentages of different products obtained. The intermediate products which do not contain a polar group are further alkylated with a 1-alkene having one polar group whereby residual phosphine hydrogen atoms are replaced by alkyl groups containing a polar group. These alkylated phosphines are then oxidized to the corresponding oxides. The three step reaction scheme is illustrated in Table 2 based on the ethylenically unsaturated cyclic hydrocarbon norbornene and allyl alcohol (2-propene-1-ol). Although a number of products are possible, the predominant oxidized product (about 80%) had a composition of two moles of norbornene and are mole of allyl alcohol. Additional products of this invention are shown in Table 1.

Exemplary ethylenically unsaturated hydrocarbons used as intermediates herein include norbornene, 5-vinyl-2-norbornene 2,5-norbornadiene, 5-ethylidene-2-norbornene, camphene, alpha-pinene, dicyclopentadiene, terpineol and geraniol.

Some exemplary 1-alkenes containing a polar group are set forth in the following list:

$CH_2=CH-CH_2CONH_2$
$CH_2=CH-CH_2CONHCH_3$
$CH_2=CH-CH_2OH$
$CH_2=CH-CH_2CH_2CH_2OH$
$CH_2=CH-CH_2CH_2NH_2$
$CH_2=CH-CH_2CH_2NHC_2H_5$
$CH_2=CH-CH_2CH_2COOC_2H_5$
$CH_2=CH-CH_2NH_2$
$CH_2=CH-CH_2SO_2OC_2H_5$ $$CH_2=C\overset{\overset{CH_3}{|}}{H}CH_2CH_2OH$$

$CH_2=CHCH_2CONHCH_2NHCOCH_2CH=CH_2$ $$CH_2=CH-\overset{\overset{C_2H_5}{|}}{C}HCONH_2$$

$CH_2=CH-CH_2COOC_4H_9$
$CH_2=CH-CN$
$CH_2=CH-COOH$
$CH_2=CH-CONH_2$
$CH_2=CH-COOCH_3$
$CH_2=CH-COOR$

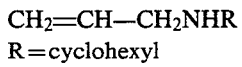

CH₂=CH—CH₂NHR

R = cyclohexyl

Free radical-yielding catalysts, suitable for use in the present reaction, are known entities and include perioxidic radical-forming agents or azobisisobutyronitrile. The substituted olefins containing an electronegative group, for example, acrylonitrile, acrylamide, acrylic acid and esters, etc., require a strongly alkaline catalyst. These bases are the oxides, hydroxides, alcoholates of the alkali metals or the alkali metals themselves. For example, an aqueous solution of potassium hydroxide, sodium hydroxide, sodium oxide, potassium methylate, etc. can be used. Also suitable are alkyl substituted nitrogen bases.

The reaction can be carried out in the reverse manner. For example, PH₃ can be reactd with acrylonitrile using aqueous potassium hydroxide to form a monocyanoethyl phosphine and subsequently reacted with a cyclic olefin using a free radical catalyst.

In preparing the phosphine oxides of this invention, the phosphine materials are formed by reacting an ethylenically unsaturated cyclic hydrocarbon or alcohol with phosphine in the presence of the radical-producing catalyst, preferably azobisisobutyronitrile. The reaction is conducted at moderately elevated temperatures, 100° C. being a practical and working temperature. It is preferred to carry out the reaction in a relatively inert, normally liquid organic solvent of which the aromatic hydrocarbons such as toluene or xylene are suitable. The proportions of unsaturated cyclic hydrocarbon or alcohol to phosphine are selected in order that the resulting phosphine will contain some free phosphine hydrogens as shown in formula I below:

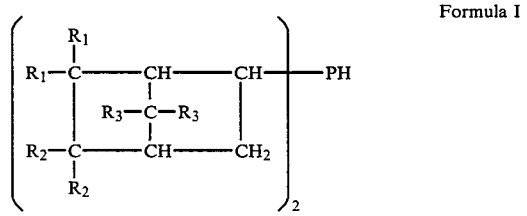

Formula I

R₁ = —H; —CH=CH₂; =CH₂; =CHCH₂

R₂ = —H; —CH₃

R₃ = —H; —CH₃

The phsophine is then alkylated in the presence of a catalyst with a 1-alkene, bearing a polar group, to give a tertiary phosphine which on oxidation, preferably with hydrogen peroxide, results in a phosphine oxide of the type herein. Using such exemplary 1-alkenes as acrylic acid, allyl alcohol, acrylonitrile and acrylamide, the cycle phosphine oxide described aforesaid would have the structure shown in formula II:

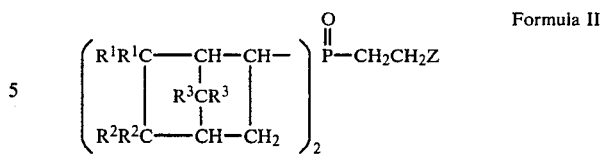

Formula II wherein $R^1$, $R^2$ and $R^3$ are in formula I and Z is —OH, —CN, CH₂—NH₂, —CONH₂ or —COOH.

The following examples further illustrate the invention.

EXAMPLE I

A two liter stainless steel pressure reactor was charged with 200 grams of toluene and 140 grams (4.1 moles) of phosphine. The reactor was sealed and heated to 105° to 110° C. This resulted in a gauge pressure of about 4.482 kPa (650 psi). A solution of 300 grams of 5-ethylidene-2-norbornene and 5 grams of azobisisobutyronitrile catalyst in 200 grams of toluene was added over a period of three hours. The temperature was controlled between 105° and 110° C. An additional 4 grams of catalyst in 100 grams of toluene was added to the reactor over a one hour period, left to stand for another hour at 105°–110° C. and then cooled to below 40° C.

The unreacted phosphine was vented from the reactor. A solution of 500 grams (8.6 moles) of allyl alcohol and 2 grams of azobisisobutyronitrile was added to the reactor which was then heated to 110° C. A mixture of 200 grams of toluene and 4 grams of azobisisobutyronitrile was added over a period of three hours then held in the reactor for an additional hour while the temperature was maintained at 105°–110° C.

The reactor was thin cooled to room temperature after which excess reactants and solvents were distilled from the product.

The residual product was oxidized with the slow addition of 614 grams of 20% hydrogen peroxide added over a period of three hours. When the exothermic reaction subsided the solution of phosphine oxide was tested by adding one drop of the solution to 1 ml of carbon disulfide until no red coloration can be detected visually in the carbon disulfide layer. This indicated complete oxidation of the phosphine to the phosphine oxide.

Following oxidation with hydrogen peroxide the volatiles were removed from the product by heating to 150° C. under 1 mm Hg vacuum. The resulting 619 grams of dried product had a phosphorus content of 11.76%. The product of this example is an effective flame retardant when added to polyphenylene ether polymers in amounts of 4 to 15 parts per hundred parts of polymer.

EXAMPLE 2

A two liter stainless steel pressure reactor was charged with 470 grams of dried norbornylene, 4 grams of azobisisobutyronitrile, 200 grams of toluene and 104 grams of toluene and sealed. The reactor was heated to 100° C. A solution of 200 grams of toluene containing 6 grams of azobisisobutyronitrile was added over a two hour period while maintaining the reactor temperature between 107° and 122° C. during which the pressure maintained was 689.5 Pa (100 psi). A solution of 470 grams of dried norbornylene, 200 grams of toluene and 4 grams of azobisisobutyronitriled was slowly added to the reactor over a 6 hour period and then cooled to below 40° C.

Unreacted phosphine was purged from the reactor which was then resealed and heated to 106° C. Four hundred grams of allyl alcohol, containing six grams of azobisisobutyronitrile was added over a two hour period. Following this, 200 grams of toluene containing 6 grams of azobisisobutyronitrile was added over a two hour period. The reactor was then cooled and 1600 grams of product was recovered.

The toluene, unreacted norbornylene and allyl alcohol were removed under vacuum. The remaining product was oxidized with a 330 gram solution of 30% hydrogen peroxide diluted with 150 grams of distilled water. Following the oxidation the water was stripped off and the product dried under vacuum for two hours at 150° C.

EXAMPLE 3

Two hundred grams of toluene, two hundred grams (2.1 moles) of norbornylene and 50 grams (0.57 moles) of 2-cyanoethyl phosphine were added to a small reactor equipped with a reflux condenser. The mixture was heated to 90° C. and a mixture of 100 grams of toluene containing 4 grams of azobisisobutyonitrile was added over a two hour period. Then the light boiling materials were distilled and removed overhead after which the residue was oxidized with 60 grams of 30% hydrogen peroxide. The dried oxidized product contained 10.92% phosphorus and had an acid number of 21.8. The approximate composition of the products produced is shown in Table 2.

TEST PROCEDURES

Flame Retardancy Tests

The oxygen index test (ASTM D-2863) employs a vertical glass tube 60 cm high and 8.4 cm in diameter in which a rod or strip specimen is held vertically by a clamp at its bottom end. A mixture of oxygen and nitrogen is metered into the bottom of the tube, passed through a bed of glass beads at the bottom to smooth the flow of gas. The sample is ignited at its upper end with a hydrogen flame, which is then withdrawn, and the sample burns like a candle from the top down. The atmosphere that permits steady burning is determined. The limiting oxygen index or simply oxygen index is the minimum fraction of oxygen in an oxygen-nitrogen mixture which will just sustain burning for two inches or three minutes, whichever comes first.

In the Underwriters Laboratory (UL)-Subject 94 vertical burn test, a sample (5.0×0.5 in.) is exposed vertically to a Bunsen burner flame for 10 seconds. The sample is ignited at the bottom and burns up. If the specimen self-extinguishes within 30 seconds, another 10 second application is made. Flaming droplets are allowed to fall on dry absorbent surgical cotton located 12 inches below the sample. If the average burning time for ten samples is less than 5 seconds and the drips do not ignite the cotton, the material is classified 94V-0. If the time is less than 25 seconds and the drips do not ignite the cotton, the material is classified 94V-1. If the sample is self-extinguishing but the cotton is ignited, the material is classified as 94V-2.

Stress Cracking Test

The specimens used in the stress cracking test are injection molded. The dimensions are 2.4"×0.5"×0.125". The Noryl bar is bent and placed in the stress jig to give approximately 1% strain. Liquid plasticizer or flame retardant to be evaluated is brushed over the middle 0.5" of the bar. Time to first visible crack and complete failure of the bar are recorded. The test is performed at room or elevated temperature.

Spiral Flow Procedure

Evaluation of plastic flow for comparison purposes is done using an injection molding machine and spiral flow mold. The mold consists of a cavity in the shape of a spiral in which flow or distance numbers in inches are inscribed in the cavity. Molten plastic enters the cavity and fills the mold's cavity. Depending on the flow characteristic of the plastic resin, the spiral will fill up more (better flow) or less (poorer flow). The flow also depends on molding profile (injection temperatures, pressures, shot size, etc.), therefore comparison of different resins are done at the same conditions. The reading of the flow is simply done by removing the molded spiral and reading off the number of inches it flows.

Extrusion Compounding

To compound polyphenylene ether polymers and additives, first a dry blend of the powdered polymer and liquid or solid flame retarding additive is prepared. The dry blend is then fed into the twin screw extruder at preselected temperatures. The resin and additives are melt compound inside the extruder where the temperature and mixing screw plasticate and mix the ingredients. The molten compound exits through a nozzle and immediately enters a cooling both (water) and is then chopped to give pellets. The pellets were molded into test pieces.

Reference is now made to Table 3 showing the physical characteristics of exemplary molded test pieces containing compounds of the invention compared to a sample containing a well known isopropylated phenyl phosphate ester flame retardant. It will be noted that the new compounds not only did not stress crack but, unlike other candidate compounds, gave very good moldings.

TABLE 1

Norbornylene/Phosphine/Allyl Alcohol
Oxidized Reaction Products where NB = norbornylene $(NB)_2-\overset{\overset{O}{\|}}{P}-CH_2CH_2CH_2OH$  $(NB)_2-\overset{\overset{O}{\|}}{P}-H$  $(NB)_3\overset{\overset{O}{\|}}{P}$

80%   15%   5%

5-ethylidene-2-norbornene/Phosphine/Allyl Alcohol
Oxidized Reaction Products where ENB = 5-ethylidene-2-norbornene $(ENB)-\underset{CH_2CH_2CH_2OH}{\overset{\overset{O}{\|}}{P}}-CH_2CH_2CH_2OH$   $(ENB)_2-\overset{\overset{O}{\|}}{P}-CH_2CH_2CH_2OH$

68%   12%

Dicyclopentadiene/Phosphine/Allyl Alcohol
Oxidized Reaction Products

TABLE 1-continued where DCP = dicyclopentadiene

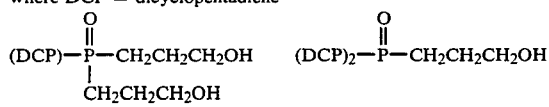

| 60% | 30% |

Norbornylene/Phosphine/Acrylonitrile
Oxidized Reaction Products where NB = norbornylene

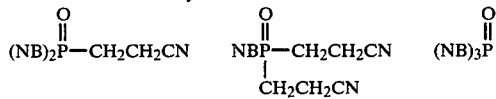

| 66% | 16% | 40% |

TABLE 2

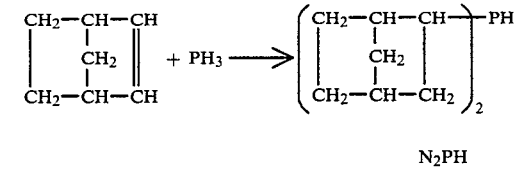

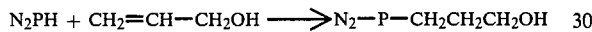

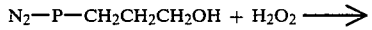

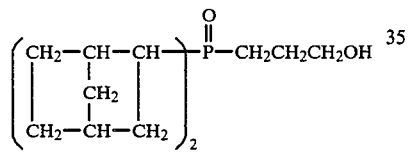

TABLE 3

| Compound | Phosphate Ester | Phosphine Oxide Norbornylene Allyl Alcohol | Phosphine Oxide Norbornylene Acrylonitrile | Phosphine Oxide ENB[(1)] Allyl Alcohol |
|---|---|---|---|---|
| FR Concentration, phr | 15 | 11.9 | 12.2 | 9.7 |
| % Phosphorus | 1.1 | 1.2 | 1.2 | 1.0 |
| Heat Distortion Temp, °F. | 163 | 185 | 183 | 212 |
| Izod Impact, Notched, in lb/in | 3.4 | 3.5 | 1.7 | 2.6 |
| Gardner Impact in lb. | 174 | 147 | 115 | 79 |
| Spiral flow, in. | 31.5 | 32.0 | — | 32.0 |
| Flammability | | | | |
| UL-94 | | | | |
| 1/16", sec. | 5.8 | 9.1 | 8.4 | 18.4 |
| ⅛", sec. | 2.1 | 2.6 | 2.5 | 6.2 |
| Flexural Strength, psi | 9100 | 11,050 | 11,280 | 10,670 |
| Flexural Modulus × 10⁵, psi | 3.15 | 3.32 | 3.35 | 3.07 |
| Stress cracking | yes | no | no | no |

* at equivalent phosphorus content, heat distortion temperatures are higher for phosphine oxides compared to phosphate esters (K-50).
* impacts about equivalent for allyl alcohol containing FR's.
* processability as measured by flow are equivalent.
* flamability about equivalent.
* phosphate ester results in stress cracking of Noryl; phosphine oxides do not stress crack.
(1) 2-ethylidene-5-norborlene.

What is claimed is:

1. A phosphine oxide compound represented by the formula:

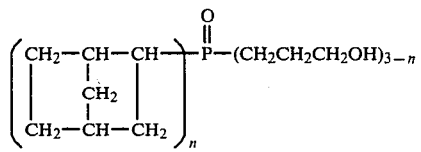

wherein P is phosphorus, O is oxygen, A is an alkylene chain of 2 to 12 carbon atoms, Z is a polar group, n is 1 or 2, and R is aan alicyclic hydrocarbon or alcohol selected from the group consisting of alpha pinene, norbornylene, norbornadiene, camphene, dicyclopentadiene, vinyl norbornylene, 5-ethylidene-2-norbornene, terpineol and geraniol.

2. The composition of claim 1 in which Z is selected from the group consisting of amino, hydroxy, amide, cyano, carboxylic acids and esters thereof and sulfonic acid and esters thereof.

3. A phosphine oxide compound of the formula

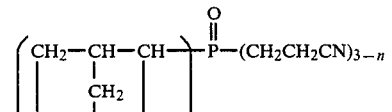

wherein n is 1 or 2.

4. A phosphine oxide compound of the formula

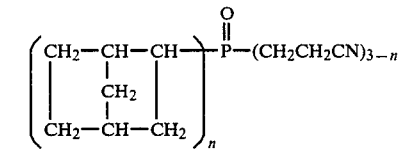

wherein n=1 or 2.

5. A phosphine oxide compound of the formula

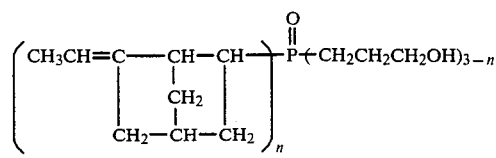

wherein n is 1 or 2.

* * * * *